United States Patent [19]

Boyle, Jr. et al.

[11] Patent Number: 4,574,060
[45] Date of Patent: Mar. 4, 1986

[54] SELECTIVE CONVERSION OF ACRYLONITRILE INTO 1,4-DICYANO-1-BUTENE CATALYZED BY POLYMER-BOUND ALKYL DIARYLPHOSPHINITES

[75] Inventors: William J. Boyle, Jr., Warren; Frank Mares, Whippany; Andrea M. Wallo, Morristown, all of N.J.

[73] Assignee: Allied Corporation, Morris Township, Morris County, N.J.

[21] Appl. No.: 438,687

[22] Filed: Nov. 3, 1982

[51] Int. Cl.$^4$ ............................................. C07C 121/30
[52] U.S. Cl. ..................................... 558/457; 525/340
[58] Field of Search ................................ 260/465.8 D

[56] References Cited

U.S. PATENT DOCUMENTS

| | | | |
|---|---|---|---|
| 4,059,542 | 11/1977 | Jennings et al. | 252/431 P |
| 4,089,890 | 5/1978 | Jennings et al. | 260/465.8 D |
| 4,100,186 | 7/1978 | Wright | 260/465.8 D |
| 4,102,915 | 7/1978 | Jennings et al. | 260/465.8 D |
| 4,126,632 | 11/1978 | Hogan et al. | 260/465.8 D |
| 4,138,428 | 2/1979 | Jennings et al. | 260/465.8 D |
| 4,190,616 | 2/1980 | Jennings et al. | 260/945 |
| 4,238,422 | 12/1980 | Cozens et al. | 260/465.8 D X |
| 4,263,224 | 4/1981 | Jennings et al. | 260/465.8 D |
| 4,316,857 | 2/1982 | Gilbert | 260/465.8 D |

OTHER PUBLICATIONS

D. Wittenberg et al., Chemical Abstracts, vol. 62 (1965), 14508e.
W. H. Dietsche, Tetrahedron Letters (1966), No. 51, pp. 6347–6351.
C. U. Pitman et al., (Chemtech, Sep. 1973, pp. 560–566).
W. O. Haag et al., Paper No. 29, in "Proc. 5th International Congress on Catalysis", vol. 1, pp. 465–472 (1973).
D. D. Whitehurst in Chemtech, Jan. 1980, pp. 44–49.
G. Manecke et al., in Makromolekulare Chem., 117, 725 (1976).
S. Nozakura et al., in J. Polymer Sci., A, 10, 2767 (1972).
Miles, J. Org. Chem. (1975), p. 40, 343.
Steininger (Chem. Ber., 1962, 95, 2993).
(T. L. Emmick et al., J. Am. Chem. Soc., 1968, 90, 3459).
S. E. Jacobson et al., JACS, (1979), 101, 6938.

Primary Examiner—Joseph Paul Brust
Attorney, Agent, or Firm—Richard C. Stewart; Gerhard H. Fuchs

[57] ABSTRACT

Selective conversion of acrylonitrile into 1,4-dicyano-1-butene by contacting a liquid phase comprising acrylonitrile with an effective amount of a polymer-bound alkyl diarylphosphinite catalyst having the formula I:

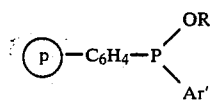

wherein the trivalent phosphorus is substituted by one alkoxy group and one aryl group and wherein the third bond of phosphorus is a P—C bond to a pendant aryl group of the polymer matrix, such as polystyrene cross-linked with divinylbenzene is disclosed. Treatment of the liquid phase, prior to contacting same with the polymer-bound catalyst, with a drying agent comprising a polymer-bound dialkyl arylphosphonite and regeneration of the drying agent are also disclosed.

16 Claims, 9 Drawing Figures

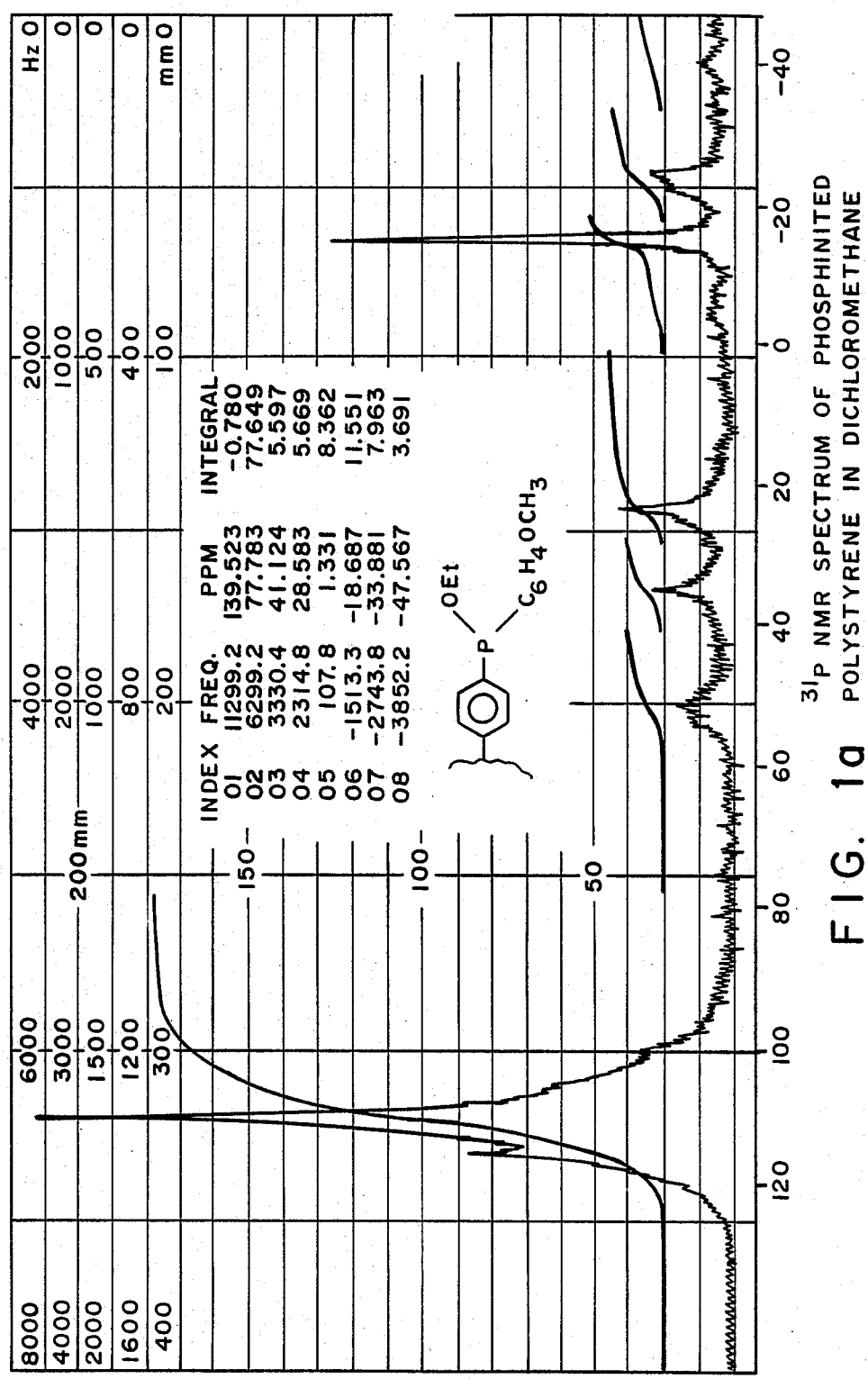
FIG. 1a  $^{31}P$ NMR SPECTRUM OF PHOSPHINITED POLYSTYRENE IN DICHLOROMETHANE

SELECTIVE CONVERSION OF ACRYLONITRILE INTO 1,4-DICYANO-1-BUTENE CATALYZED BY POLYMER-BOUND ALKYL DIARYLPHOSPHINITES

CROSS-REFERENCE TO RELATED APPLICATION

This application is related to U.S. patent application Ser. No. 438,686, filed Nov. 3, 1982 by same inventive entity and filed on even date herewith, now abandoned.

BACKGROUND OF THE INVENTION

This invention relates to the preparation of 1,4-dicyano-1-butene by contacting a liquid phase comprising acrylonitrile with an effective amount of a polymer-bound alkyl diarylphosphinite catalyst having the formula I:

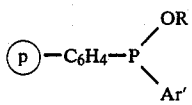

wherein the trivalent phosphorus is substituted by one alkoxy group and one aryl group and wherein the third bond of phosphorus is a P—C bond to a pendant aryl group of the polymer matrix.

The dimerization of acrylonitrile to 1,4-dicyano-1-butene has been much investigated as a route to adiponitrile which is hydrogenated to hexamethylene diamine, the nylon 6,6 monomer.

A process for the dimerization of acrylonitrile in the presence of phosphines ($PR_3$) and phosphites ($P(OR)_3$) to give a 2:1 mixture of 2,4-dicyano-1-butene and cis- and trans-1,4-dicyano-1-butenes is disclosed in C.A., Vol. 62 (1965), 14508e (D. W. Wittenberg, et al.).

Tetrahedron Letters (1966) No. 51, pp 6347-51, (W. H. Dietsche) discloses that alkyl diarylphosphinites having the formula $Ar_2POR$ in the presence of t-butanol or aqueous acetic acid effects dimerization of acrylonitrile to 2,4-dicyano-1-butene (2-methyleneglutaronitrile) and 1,4-dicyano-1-butene.

The dimerization of acrylonitrile (ACN) in the presence of various tervalent oxygen-containing phosphorus (III) catalyst compositions and a mixture of a hydrocarbon such as toluene and a proton-donating solvent such as 2-propanol has been disclosed in a series of U.S. patents granted to personnel of Imperial Chemical Industries (ICI).

U.S. Pat. No. 4,102,915 (Jennings et al.) discloses that a process for dimerization of ACN to substantially linear C, dimers using homogeneous, i.e., soluble organic phosphinites or phosphonites as catalysts, is effected in the presence of a proton-donating solvent and optionally a hydrocarbon co-solvent, wherein ACN and solvents are dry and free of oxygen and wherein at least one of the solvents has a boiling point higher than ACN and is capable of phase separation with respect to dimeric products, to enable unreacted ACN to be removed by distillation and the solvent(s) and dimeric products to be separated.

U.S. Pat. No. 4,316,857 (Gilbert) discloses a soluble phosphonite or phosphinite catalyzed ACN dimerization process that uses as a solvent a mixture of a proton-donating organic solvent, an aromatic hydrocarbon solvent and an aliphatic hydrocarbon solvent in a specified ratio so as to facilitate product isolation such as by phase separation or liquid extraction.

U.S. Pat. No. 4,238,422 (Cozens et al.) discloses soluble aryl phosphinites and phosphonites useful as ACN dimerization catalysts wherein the aryl groups are substituted by at least one electron-donating group.

U.S. Pat. Nos. 4,138,428 and 4,190,616 (Jennings et al.,) disclose ACN dimerization process and soluble organic phosphinite or phosphonite catalysts having at least one aryl group substituted by electron-donating substituents.

U.S. Pat. No. 4,263,224 (Jennings et al.) discloses ACN dimerization process wherein an aryl phosphonite or phosphinite is added as a low-cost scavenging reagent to a mixture of ACN and organic solvent to remove therefrom residual traces of water or other catalyst deactivating impurities before contacting said reaction mixture with a more expensive soluble aryl phosphinite or aryl phosphonite dimerization catalyst.

U.S. Pat. No. 4,126,632 (Hogan et al.) discloses a process for the dimerization of ACN to straight chain 1,4-dicyanobutenes by contacting ACN with organic phosphinite or phosphonite catalyst having the formula $R_1R_2R_3P$ or $(R_1R_2P)_2R_4$ wherein at least one of the R groups $R_2$ or $R_3$ is alkoxy or cycloalkoxy and $R_4$ is alkylene or alkylenedioxy in the presence of an inert proton-donating solvent and optionally an inert hydrocarbon co-solvent. While this patent also provides examples of soluble phosphinites and phosphonite wherein groups $R_1$ to $R_4$ are alkyl, aryl, cycloalkyl, polyalkylene, etc., the patent also discloses without examples that groups $R_1$ to $R_4$ may also be part of a polymeric backbone, for example, polystyrene or polyvinylalcohol or be linked to an inorganic support, for example, silica or alumina, so as to form a heterogeneous catalyst.

U.S. Pat. Nos. 4,059,542 and 4,089,890 (Jennings, et al.) disclose that silica- or alumina-bound phosphinites or phosphonites as heterogeneous, i.e., insoluble catalyst compositions may only be used for the gas-phase dimerization of acrylonitrile at temperatures above 150° C. When the best phosphinite-bound to silica catalyst disclosed in U.S. Pat. Nos. 4,059,542 and 4,089,890 was employed for dimerization of ACN in the gas phase at 170°-190° C., only low conversions (7-20%) of ACN into an economically unattractive 3:1 (maximum value) mixture of straight and branched chain dimers and an unspecified amount of oligomers were observed.

The processes using soluble catalysts disclosed in these ICI patents produced 1,4-dicyanobutene, the desired linear dimer, at moderate conversions, in high selectivity with lesser amounts of the branched dimer, methyleneglutaronitrile and oligomers. However, the ACN dimerization processes employing homogeneous, i.e., soluble alkyl diarylphosphinites substituted by electron-donating groups have the following disadvantages. At the end of each ACN dimerization run, before distillation of the desired dimeric products, the soluble phosphinite catalyst must either be removed by complicated extraction procedures or decomposed with water. The extraction procedures inherently result in appreciable losses of the soluble phosphinite catalysts for two reasons. Firstly, the differences in the solubility of the soluble phosphinite catalyst in the solvents are not infinite, and thus, several extractions of the catalyst are required. Secondly, extraction enhances the chances for contamination of the solvents, unreacted ACN and catalyst with moisture and oxygen, impurities which deactivate the catalyst. Decomposition of the soluble phosphinite catalyst by the addition of water substantially increases catalyst consumption and contaminates the reaction solvents (isopropanol and toluene) and unreacted ACN with water and/or oxygen. Thus, after extraction and decomposition procedures, the reaction solvents and unreacted ACN must be degassed and redried before the recycle of same. In the case of isopropanol and ACN, degassing and redrying are very costly and time consuming steps.

One way in which the workup of the dimerization reaction could be greatly simplified, while simultaneously conserving the expensive catalyst, would be to support the catalyst on a polymer matrix. C. U. Pitman, et al. (CHEMTECH, September 1973, pp 560–566) Pitman, et al. (CHEMTECH, September 1973, pp 560–566) disclose that soluble catalysts, e.g., transition metal catalyst, may be bound to polymer backbones. See also Paper No. 29 by W. O. Haag, et al., in "Proc. 5th International Congress on Catalysis", Vol. 1, pp 465–472 (1973) and an article by D. D. Whitehurst in CHEMTECH, January, 1980, pp. 44–49.

During the course of development of the present invention, phosphinites bound to organic polymer matrices via P—O—C bonds were repared and were found to be impractical and inactive catalysts for ACN dimerization. Similarly, phosphinites bound via P—O—M bonds to inorganic matrices (M), as disclosed in U.S. Pat. Nos. 4,089,890 and 4,059,542 (ICI), possess a low activity and low selectivity and may be used only for gas phase ACN dimerizations. Although the above-identified ICI U.S. Patents mention the use of polystyrene-bound phosphinites, no working example of the use and/or preparation of same is given in the above-identified ICI U.S. Patents or in other published literature of which we are aware.

Accordingly, it is an object of the present invention to provide an ACN dimerization process that employs a heterogeneous catalyst that avoids the complicated workup and product isolation procedures of prior art while preserving the integrity of the catalyst.

These and other objects and advantages of the present invention will become obvious in view of the following description.

SUMMARY OF THE INVENTION

According to an object of the present invention, we provide a process for conversion of acrylonitrile into 1,4-dicyano-1-butene which comprises contacting a liquid phase comprising acrylonitrile with an effective amount of a polymer-bound alkyl diarylphosphinite catalyst having the formula I:

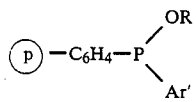

wherein the trivalent phosphorus is substituted by one alkoxy group and one aryl group and wherein the third bond of phosphorus is a P—C bond to a pendant aryl group of the polymer matrix for a time sufficient to effect conversion to a stream containing 1,4-dicyano-1-butene.

BRIEF DESCRIPTION OF THE DRAWINGS

FIGS. 1a and 1b are $^{31}$P NMR Spectra of preferred embodiments of a polymer-bound phosphinite catalyst of the present invention.

DETAILED DESCRIPTION OF THE INVENTION

Figure 1B:
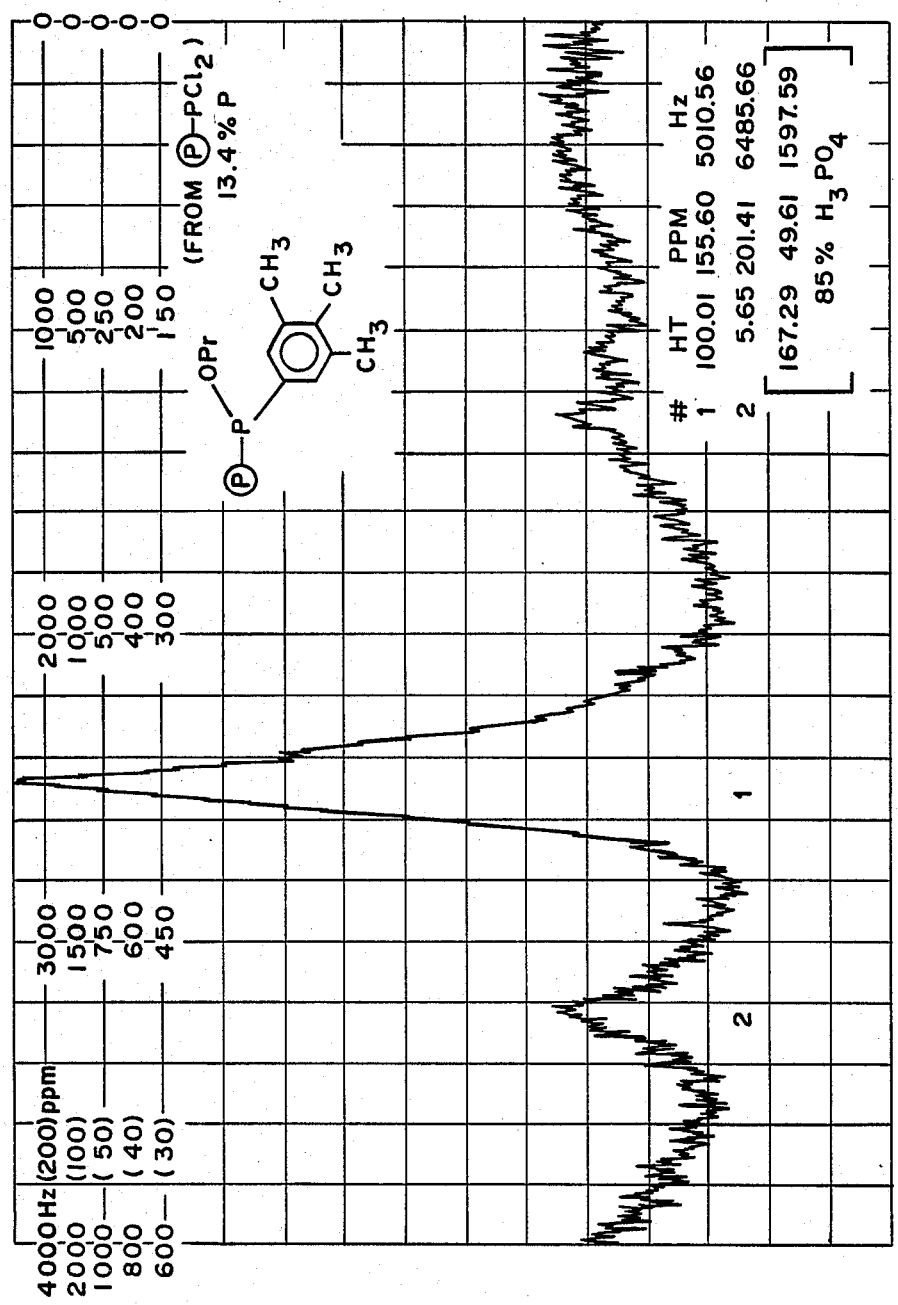

The present invention provides a process for dimerization of acrylonitrile that may be operated batchwise or continuously with high selectivity and high percent conversion by contacting a liquid phase comprising acrylonitrile, at least one inert solvent, and a proton-donating solvent with a polymer-bound alkyl diarylphosphinite catalyst having formula I, positioned in a fixed bed or in a flow reactor, for a time sufficient to effect conversion of ACN to a stream containing 1,4-dicyano-1-butene. Thus, the dimerization process using the polymer-bound catalyst composition of the present invention affords batchwise or continuous operation, facile product separation and recovering of same from the reaction medium and recycling of unreacted acrylonitrile and inert proton-donating solvents while maintaining high selectivity to the preferred linear dimer, 1,4-dicyano-1-butene at a high conversion of ACN. Further, the immobilization of the phosphinite catalyst on a polymer matrix eliminates the need for complicated workup procedures of the prior art and minimizes degradation of expensive active catalysts by exposure of same to water and air.

In batchwise operation, the polymer-bound phosphinite catalyst is separated by a simple filtration; in continuous operation, no separation is necessary because the effluent from the flow reactor is free of catalyst. In either case, the converted acrylonitrile comprising linear and branched chain dimers and oligomers are conveniently and easily separated from the unreacted acrylonitrile, at least one inert hydrocarbon and proton-donating solvent by a simple distillation. The condensed volatile components—unreacted acrylonitrile, at least one inert hydrocarbon solvent and a proton-donating solvent—can be recycled to a batch or continuous reactor without any further purification because contamination of the condensed volatile components by water or oxygen has been practically eliminated.

In a preferred embodiment of the present invention, dimerization of acrylonitrile was effected continuously over 184 hours using a flow reactor packed with a preferred embodiment of the polymer-bound catalyst having formula I wherein R=ethyl or isopropyl and Ar'-=p—CH$_3$OC$_6$H$_4$—, i.e., with ⓟ—C$_6$H$_4$—P(p—CH$_3$OC$_6$H$_4$—)O—C$_2$H$_5$ or ⓟ—C$_6$H$_4$—P(p—CH$_3$OC$_6$H$_4$—)O—i—C$_3$H$_7$. The percent conversion slowly declined from 63% initially to 40% at 184 hours. The percent selectivity to linear and branched dimers was 90-91% (92% linear, 8% branched).

In contradistinction thereto, trimethylsilyldibutylphosphinite, a soluble phosphinite having a P—O—Si bond and serving as a model compound for the phosphinites bound to silica such as disclosed in U.S. Pat. Nos. 4,059,542 and 4,089,890, I was prepared (See Example 18), and was tested as an ACN dimerization catalyst (see Example 19) but was found completely inactive and was, in a relatively short time (3 hrs) in the ACN dimerization medium, converted into an catalytically inactive phosphorus (V) species. Partially phosphinated derivatives of polyvinyl alcohol and of various hydroxylcontaining polymers were prepared and showed little or no activity as ACN dimerization catalyst, in agreement with the results of other studies conducted with 1,2- and 1,3-diols, which are not reported in the experimental section herein below. (See Comparative Example 28 and Table V). Fully phosphinited derivatives of hydroxylcontaining polymers required addition of proton donors, e.g., isopropanol or neopentyl alcohol to the ACN dimerization medium. The presence of such proton donors caused solvolysis of the polymer-bound phosphinites and the formation of soluble monomeric phosphinites. See Table V for a summary of these results.

Phosphinite bound to polyvinyl alcohol (PVA), PVA cross-linked with TDI and similar OH-containing polymers such as 4-(2-hydroxypropyl)polystyrene and "TOYOPEARL", a trade name for a PVA cross-linked copolymer containing aliphatic hydroxyl and non-hydroxyl oxygen moities, were found to be impractical or ineffective catalysts for ACN dimerization.

Figure 2:
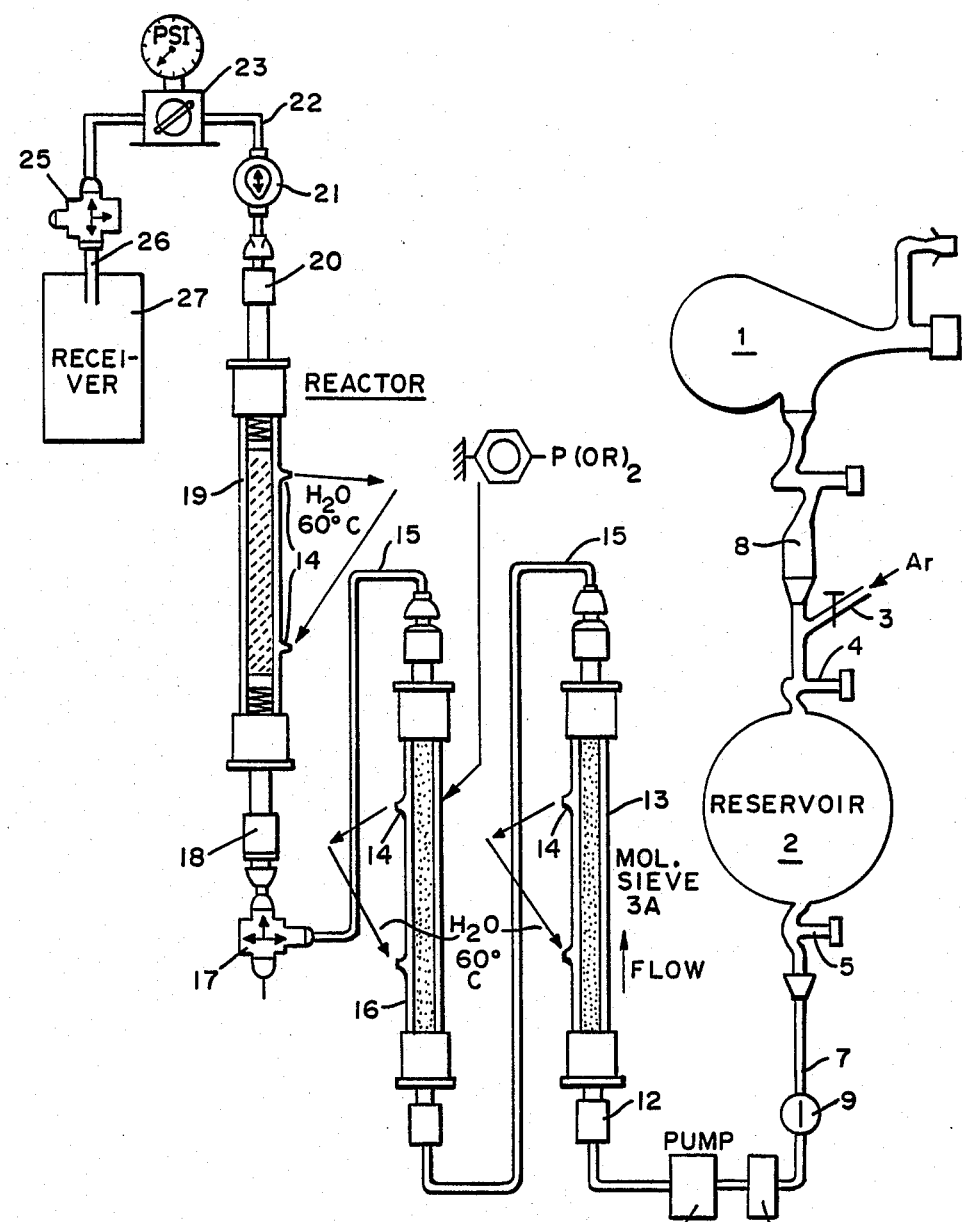
FIG. 2 schematically illustrates operation of the polymer-bound phosphinite catalyst of the present invention in a flow reactor.

In another preferred embodiment of the present invention, the liquid phase comprising acrylonitrile, at least one inert solvent and a proton-donating solvent and containing less than 30 ppm, preferably less than 15 ppm water, is contacted prior to contact with the polymer-bound phosphinite catalyst, with a recyclable polymer-bound dialkyl arylphosphonite which lowers the water content to 5 ppm or less. The polymer-bound phosphonite is conveniently contained in a fixed bed, i.e., column such as illustrated in FIG. 2, and may be recycled, i.e., reconverted to phosphonite by scheme illustrated in FIG. 6.

By the term "% conversion", as used herein, is meant the % by weight of acrylonitrile (ACN) that is converted to total linear/branched dimeric, oligomeric and polymeric products.

By the term "% selectivity", as used herein, is meant the % by moles of acrylonitrile converted into linear dimers, i.e., cis- and trans-1,4-dicyano-1-butene (DCB-1). Thus, % selectivity is defined as twice the number of moles of DCB-1 divided by moles of reacted acrylonitrile multiplied by 100%.

The liquid phase comprising acrylonitrile that is contacted with the polymer-bound alkyl diarylphosphinite further comprises at least one inert solvent and a proton-donating compound. The concentration (% by volume) of acrylonitrile in the liquid phase is not critical and is conveniently adjusted between about 5% and 50% to control the rate of reaction. Concentrations of acrylonitrile above about 50% in liquid phase lead to oligomer and polymer formation and should be avoided. When the concentration of acrylonitrile is below about 5% in liquid phase, the reaction rate is too low to be practical.

Inert solvents are those compounds which do not react or interfere with the process or catalyst or reactants of the present invention. The inert solvents found useful in the present invention are liquid, nonhydroxylic aromatic hydrocarbon solvents, including hydrocarbons such as benzene, xylenes, toluene, and polyalkylbenzenes. Toluene is the preferred inert solvent solely for economic reasons.

Mixtures of liquid aromatic hydrocarbons and different amounts of liquid aliphatic hydrocarbons may be used without interfering with the process of the present invention so long as the liquid phase remains homogeneous. Thus, aliphatic or alicyclic hydrocarbons such as petroleum ether or cyclohexane may be used with sufficient amounts of aromatic hydrocarbon(s), preferably toluene, to insure the solubility of the proton-donating solvents. Solvents such as ethers and nitriles may also be used. However, the selectivity to the desired linear dimer is decreased when the liquid phase contains polar solvents, and use of such solvents is to be avoided.

Proton-donating solvents such as aliphatic or cyclic alcohols are added to facilitate the selectivity of the dimerization process of the present invention. Proton-donating solvents of higher acidity than alcohols such as organic carboxylic or sulfonic acids, as well as thiols and phenols, interfere with the catalyst and must be avoided.

Secondary aliphatic groups having 3-10 carbons and cyclic secondary alcohols having 5 to 10 carbon atoms are preferred. Primary alcohols are found to effect dimerization of ACN, but the % selectivity is lower compared to the process employing secondary alcohols. Use of primary alcohols is less preferred. Tertiary alcohols interact with the polymer-bound phosphinite catalyst to form t-alkyl phosphinites which eliminate olefins leaving behind catalytically inactive secondary phosphine oxides. Thus, the use of tertiary alcohols is to be avoided.

Since a fixed bed or flow system, preferably a flow system, is employed, only the ratio of proton-donating solvent, preferably isopropanol:inert solvent, preferably toluene:acrylonitrile can be specified. The ratio (volume) of proton-donating solvent to inert solvent to acrylonitrile in the liquid phase is about 0.2-10:10-0.1-7.5. In the preferred embodiment of the present invention, the ratio (volume) of isopropanol to toluene to acrylonitrile is about 1:10:3. A portion of toluene may be conveniently replaced by cyclohexane and hexamethylbenzene (internal standards).

The contact time is sufficient to convert about 5-95%, preferably about 30-80% of the acrylonitrile, into the desired dimeric product. Contact times may conveniently be from about 10 minutes to about several hours.

Figure 8:
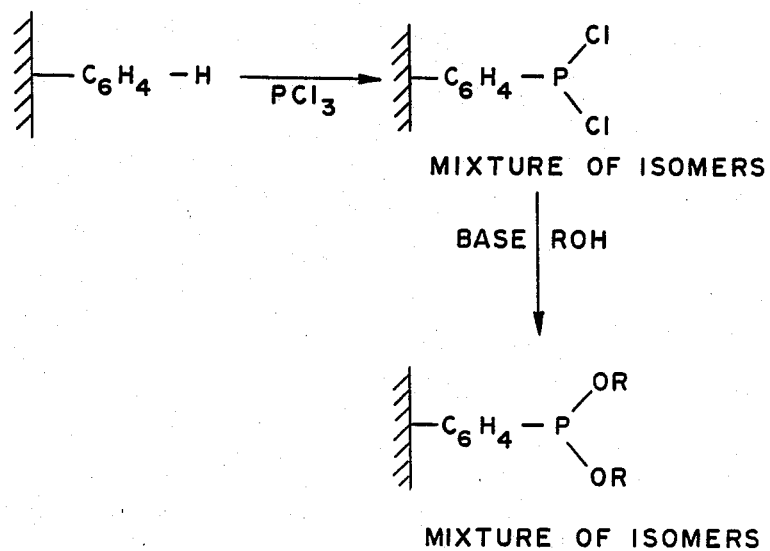
FIG. 8 schematically illustrates a preferred method of preparation of the polymer-bound dialkyl phosphonite of the present invention.

The presence of water and oxygen interferes with the process or catalyst of the present invention and must be avoided. Thus, acrylonitrile, the inert and proton-donating solvents and reactor must be rigorously dried before use. The contacting of ACN with the catalyst of the present invention is performed under substantially anhydrous conditions, i.e., the concentration of water in liquid phase is preferably maintained less than about 30 ppm, and more preferably less than about 15 ppm, and most preferably less than 5 ppm. Conventional drying agents, such as CaH$_2$, 3 A or 4 A molecular sieves, and polymer-bound dialkyl arylphosphonites having the formula II, ⓟ —C$_6$H$_4$—P(OR)$_2$, may be employed to dry the liquid phase before the start of the reaction to a value less than 5 ppm. The dimerization process of the present invention should be operated under a dry inert atmosphere, e.g., nitrogen gas, to avoid contamination by oxygen, water vapor, etc. during the operation of the process of the present invention. Stabilizers normally present in acrylonitrile such as hydroquinones or phenol-type compounds are to be removed before contacting with the catalyst in the process of the present invention. In addition, scavenging agents, such as aryl phosphonites that are disclosed in U.S. Pat. No. 4,263,224, may be conveniently added to liquid phase reservoirs prior to contacting same with polymer-bound alkyl diarylphosphinite catalyst of the present invention. Concentrations of less than one % by volume in the liquid phase of the scavenger agents are normally sufficient to remove chemicals such as H$_2$O that would adversely affect the polymer-bound catalyst of the present invention. In a preferred embodiment of the present invention, polymer-bound dialkyl arylphosphonites having the formula II, ⓟ —C$_6$H$_4$—P(OR)$_2$ wherein R is an aliphatic group of 1 to 10 carbons or cyclic secondary group of 5 to 10 carbons, preferably a secondary aliphatic group such as isopropyl, are used to lower the water content of the liquid phase that contains acrylonitrile, inert solvent, and proton-donating solvent, and that has been subjected to conventional drying by reagents such as CaH$_2$ and molecular sieves, to a value of less than about 15 ppm, preferably about 5 ppm or lower, i.e., 2-3 ppm. The preparation of the polymer-bound dialkyl arylphosphonites is shown schematically in FIG. 8. See Example 13 hereinbelow. Levels of water in excess of 50 ppm in the liquid phase may be tolerated. However, lower selectivities and deactivation of large amounts of catalysts are to be expected.

Figure 6:
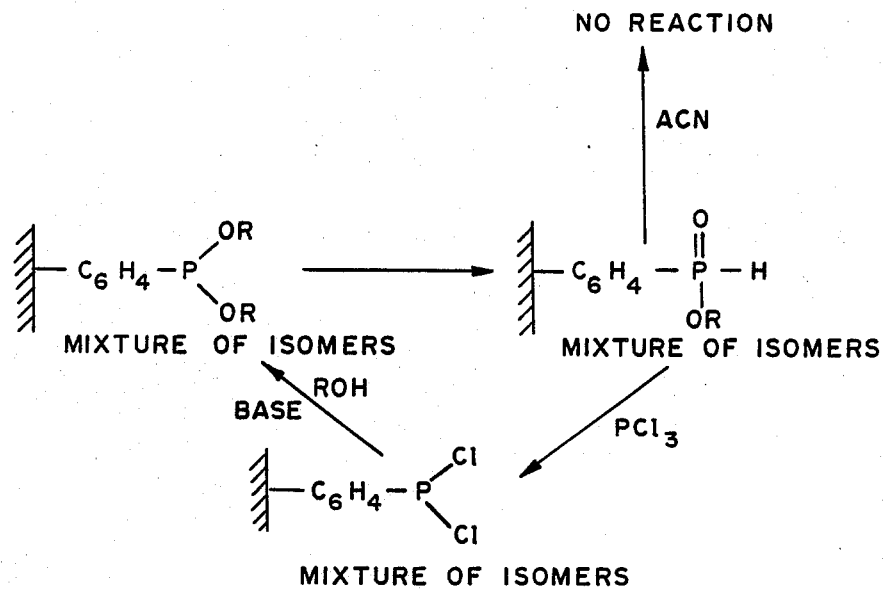
FIG. 6 schematiclly illustrates the reaction of a polymer-bound dialkyl arylphosphonite with water to form a product that does not react with ACN.
Figure 7:
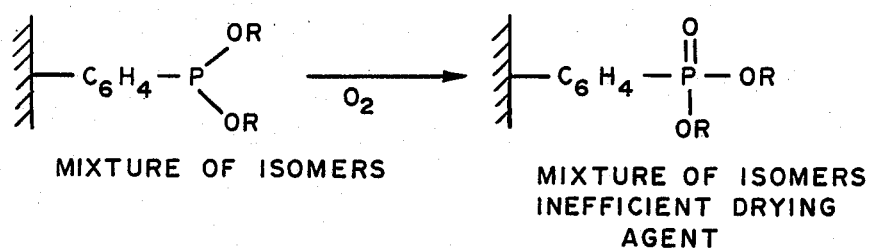
FIG. 7 schematically illustrates the reaction of polymer-bound dialkyl phosphonite with oxygen to form catalycally inactive phosphorus V.

It is a special feature of the process of the present invention that the drying agent comprising polymer-bound dialkyl phosphonite reacts with water to form a polymer-bound alkyl phosphinate having the formula ⓟ —C$_6$H$_4$—P=O(OR)(H) that does not react with ACN but that may be conveniently reconverted into polymer-bound dialkyl arylphosphonite by a sequence of steps outlined in FIG. 6. It is another special feature of the process of the present invention that the sequence of steps outlined in FIG. 6 may be performed without removing same from the container used to dry the ACN dimerization reaction medium. The polymer-bound phosphinate having the formula ⓟ —C$_6$H$_4$—P=O(OR)(H) may conveniently be treated with a reagent such as PX$_3$, COX$_2$, wherein X is halogen, preferably PCl$_3$, for a time sufficient to produce a polymer-bound alkyl arylphosphonous dichloride having the formula ⓟ —C$_6$H$_4$—P(Cl)$_2$. The polymer-bound phosphonus dichloride is then treated with a primary or secondary alcohol in the presence of a base, such as pyridine, for a time sufficient to produce a polymer-bound dialkyl arylphosphonite. The preferred alkanol is isopropanol. The preferred polymer is polystyrene cross-linked with at least about 1 to 40 weight percent divinylbenzene and having the form of micro- or macroreticular beads or clusters of beads.

The reaction temperature for ACN dimerizations of the present invention is commonly in the range of about 0° C. to 100° C. Temperatures in the range of 50° C. to about 75° C. are preferred. A temperature of about 60° C. is more preferred.

Reaction pressure is not critical and may be sub- or super-atmospheric as well as atmospheric. When the polymer-bound catalyst operates in a flow reactor, at temperatures above 50° C., super-atmospheric pressures are commonly in the range of 1–5 atm, and preferably, about 1.5–3 atm.

The polymer-bound catalyst of the present reaction comprises a polymer-bound alkyl diarylphosphinite having the formula I, ⓟ —C$_6$H$_4$—P(Ar')OR wherein the trivalent phosphorus is substituted by one alkoxy group and one aryl group and wherein the third bond of phosphorus is a P—C bond to a pendant aryl group of the polymer matrix. Among the polymers of the polymer-bound catalyst found useful in the present invention are polystyrene and polystyrene cross-linked with about 1 to 40 percent by weight of divinylbenzene and in the form of micro- or macroreticular beads or clusters of beads. Preferably, the polymer of polymer-bound catalyst comprises polystyrene cross-linked with about 1 percent of divinylbenzene.

By the term "effective amount of polymer-bound catalyst", as used herein, is meant that at least 1% of the pendant aryl groups of formula I is substituted with phosphorus in the form of phosphinite. Conveniently, at least about 5 to about 100% of the pendant aromatic rings bound to polymer backbone are substituted by phosphorus. In the preferred mode of preparation of polymer-bound catalyst of the present invention, at least about 25–100%, preferably 80% or more of the phosphorus bound to the aromatic rings were in the form of phosphinite.

The aromatic ring (Ar') bound only to phosphorus in the polymer-bound alkyl diarylphosphinite has the formula:

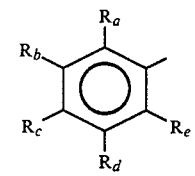

where at least one of the $R_{a-e}$ groups is an heteroatom-containing electron-donating group selected from the group consisting of —OR$^3$ and —N(R$^4$,R$^5$) wherein R$^3$, R$^4$ and R$^5$ are independently straight or branched chain alkyl groups having 1 to 10 carbons or cycloalkyl groups having 5 to 10 carbons or wherein $R_a$, $R_b$, $R_c$, $R_d$ and $R_e$ are independently selected from the group consisting of said heteroatom-containing electron-donating groups, hydrogen, straight and branched chain alkyl groups having 1 to 10 carbons and cycloalkyl groups having 5 to 10 carbons or wherein two of said $R_{a-e}$ groups form part of a fused alicyclic system and the remainder of said $R_{a-e}$ groups are independently said heteroatom-containing electrondonating groups or hydrogen or a straight or branched chain alkyl groups of 1 to 10 carbons or cyaloakyl groups of 5 to 10 carbons. Aromatic rings containing at least one heteroatom-containing electron-donating groups or three alkyl groups are preferred. Aromatic rings containing only H are less preferred.

Among the heteroatom-containing electron-donating groups found useful in the catalyst of the present invention are alkoxy ($OR^3$), N,N-dialkylamino $-N(R^4, R^5)$ wherein the alkyl groups $R^3$, $R^4$, $R^5$ are straight or branched chain aliphatic groups of 1 to 10 carbons or cycloalkyl groups of 5 to 10 carbons. Preferred heteroatom-containing electron-donating groups are $CH_3O-$, $C_2H_5O-$, $i-C_3H_7O-$, $(CH_3)_2N-$, $(C_2H_5)_2N-$, and $(n-C_3H_7)_2N-$.

Among the aromatic groups attached only to phosphorus that are useful in polymer-bound alkyl diarylphosphinite catalyst of the present invention are p-alkoxylphenyl, p-N,N-dialkylaminophenyl, 2,3,4,5-tetraalkylphenyl; 3,4,5-, 2,3,5-, 2,4,5- and 2,3,4-trialkylphenyl wherein alkyl has one to ten carbons and is preferably methyl.

The polymer-bound alkyl diarylphosphinite catalysts of the present invention contain at least 1% of the pendant aromatic groups of the polymer matrix, bound to phosphorus and substantially free of C=O groups such as e.g., aldehydes, ketones, esters and amides, or $-OH$, NHR or $-NH_2$ or SH that may react with phosphinite phosphorus or otherwise interfere with activity of the phosphinite as a selective acrylonitrile dimerization catalyst. Preferred polymer-bound catalysts of the present invention include ⓟ$-C_6H_4-P(p-CH_3OC_6H_4-)OR$, ⓟ$-C_6H_4-P[(CH_3)_3C_6H_2-]OR$; wherein ⓟ$-C_6H_4-$ is derived from a polymer which comprises polystyrene matrix and preferably, which consists essentially of polystyrene cross-linked with at least about 1 weight % of divinylbenzene and more preferably polystyrene cross-linked with at least about 1-40 weight % of divinylbenzene and in the form of micro- or macro-reticular beads or clusters; and wherein R is selected from the group consisting of straight and branched chain aliphatic groups of one to ten carbons and cyclic groups having five to ten carbon atoms. Preferred R groups are cyclohexyl, methyl, ethyl and groups having formula $R^1R^2C(H)-$ wherein $R^1$ and $R^2$ are independently selected from hydrogen and straight and branched chain alkyl groups having 1 to 9 carbon atoms such as isopropyl.

Figure 4:
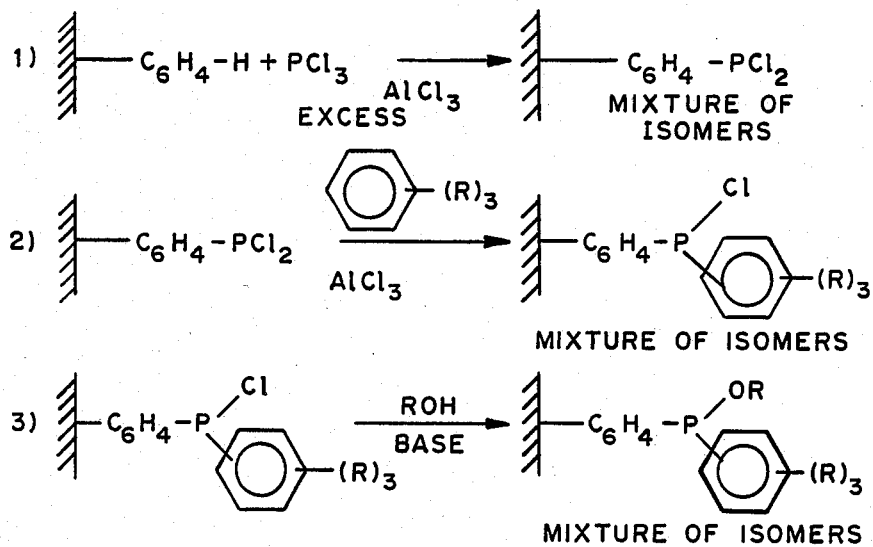
FIG. 4 schematically illustrates one synthetic pathway for preparation of a polymer-bound alkyl diarylphosphinite catalyst of the present invention.
Figure 5:
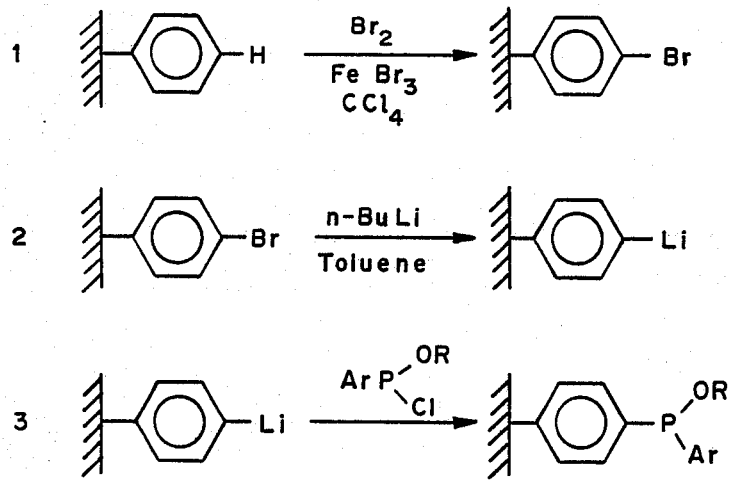
FIG. 5 schematically illustrates another synthetic pathway for preparation of a polymer-bound alkyl diarylphosphinite catalyst of the present invention.

Synthetic pathways for the preparation of the polymer-bound alkyl diarylphosphinite catalysts of the present invention are schematically illustrated in FIGS. 4 and 5. See also Examples 7 and 15 hereinbelow.

GENERAL EXPERIMENTAL

Infrared spectra, as either neat films or KBr pellets, were recorded on a Perkin-Elmer 283 Spectrophotometer. Proton, $^{13}C$ and $^{31}P$ NMR were recorded on Varian T-60, FT-80A, and XL-200 instruments. Phosphorus chemical shifts are reported relative to external 85% phosphoric acid. Gas chromatographic analyses were performed on a Hewlett Packard 5710 using a 3'×⅛" Porapak P column and a Hewlett Packard 3352B computer to monitor the retention times and peak areas.

All dimerization runs and the preparation of the polymer-bound catalysts were carried out with the careful exclusion of oxygen and moisture. Transfer of moisture-sensitive solids was carried out in a Vacuum Atmospheres Dry Box. Volatile liquids were transferred on a vacuum line, while the nonvolatile, soluble catalysts were transferred via syringe in a stream of argon.

Materials

All solvents were reagent grade. Toluene and cyclohexane were stored over sodium-potassium alloy under vacuum. Tetrahydrofuran (THF) was stirred with lithium aluminum hydride, then distilled into a solvent reservoir containing sodium-potassium alloy and anthracene. The THF was distilled from the solution of the blue radical anion as needed. Isopropanol, tert-butyl alcohol and acrylonitrile were refluxed over calcium hydride ($-40$ mesh) for at least three hours, then distilled onto flame-dried 4A molecular sieves for storage. Neopentyl alcohol was sublimed onto flamed-dried 4A molecular sieves. After standing overnight, these reagents were sampled for water content (Karl Fisher) and found to contain <30 ppm of water. Samples were taken periodically to assure that the water content remained low, i.e., less than 50 ppm. Pyridine was also dried over calcium hydride and distilled onto molecular sieves.

"TOYOPEARL ® 55", the trade name for a polyvinyl alcohol cross-linked copolymer containing aliphatic hydroxy and non-hydroxy oxygen moieties, was obtained in the form of beads as a water slurry in superfine (20–30 μm) and coarse (50–100 μm) grades from MCB, and was washed repeatedly with water and with acetone, then dried in vacuo at 100° C. for at least 24 hrs. Polyvinyl alcohol (88% hydrolyzed, avg MW 10,000) was obtained from Aldrich. Ethylene vinyl alcohol copolymer (40/60) type F was purchased from Kuraray Co., Ltd. Polyvinyl alcohol cross-linked with terephthalaldehyde and with tolylene diisocyanate were prepared as described by G. Manecke et al., in Makromolekulare Chem., 117, 725 (1976) and by S. Nozakura et al. in J. Polymer Sci., A, 10, 2767 (1972).

EXAMPLE 1

Preparation of Di-p-tolylphosphinites

Ethyl and isopropyl di-p-tolylphosphinites were prepared following the procedure of Coezens, et al., as disclosed in U.S. Pat. No. 4,238,422 at Col. 8, lines 19–59, by the reaction of ethyl or isopropyl phosphonodichloridite with p-tolylmagnesium bromide in THF. After treatment with pyridine to precipitate the magnesium halide complex, the product was purified by Kugelrohr distillation at 120°–125° C. (0.1 mmHg). Ethyl di-p-tolylphosphinite was also prepared from di-p-tolylphosphinous chloride by the procedure described in the following entry. IR (neat) 1600, 1498, 1385, 1090, 1045, 817, 520 cm$^{-1}$; $^1$H NMR (CDCl$_3$) δ7.6–7.0 (m, 8H), 3.9 (m, 2H), 2.32 (s, 6H), 1.28 (t, 3H).

EXAMPLE 2

Preparation of Ethyl Diphenylphosphinite

A solution of diphenylphosphinous chloride (135 mmol) in dry ether (120 mL) was treated dropwise at 5° C. with a solution of ethanol (200 mmol) and pyridine (134 mmol) in ether (120 mL). After addition was complete, the mixture was warmed to room temperature, filtered under argon, and the solid hydrochloride washed with ether. Evaporation of the solvent gave an oil which was purified by Kugelrohr distillation at 95° C. (0.1 mmHg). Yield: 119 mmol (88%); $^1$H NMR (CDCl$_3$) δ7.6–7.2 (m, 10H), 3.95 (doublet of quartets, $J_{H-H}=7$ Hz, $J_{P-H}=10$ Hz, 2H), 1.30 (t, J=7 Hz, 3H).

EXAMPLE 3 p-Anisylphosphonous Dichloride and Diisopropyl p-Anisylphosphonite

The phosphonous dichloride was prepared by the stannous chloride-catalyzed Friedal-Crafts reaction of phosphorus trichloride (three-fold excess) and anisole following the procedure of Miles and co-workers (J. Org. Chem., 1975, 40, 343). IR (neat) 1590, 1500, 1295, 1255, 1180, 1095, 1030, 830 cm$^{-1}$; $^1$H NMR (CDCl$_3$) 8.0-7.6 (broad t, 2H), 7.1-6.8 (broad d, 2H), 3.83 (s, 3H). The dichloride (26 mmol) was treated in dry ether with isopropanol (62 mmol) and dimethylaniline (48 mmol) at 0° C. Workup and Kugelrohr distillation at 105°-110° C. (0.05 mmHg) afforded a 53% yield of the phosphonite. IR (neat 1590, 1498, 1245, 1100, 955, 860, 750 cm$^{-1}$; $^1$H NMR (CDCl$_3$) δ7.7-7.4 (m 2H), 7.1-6.8 (m, 2H), 4.3 (m, 2H), 3.78 (s, 3H), 1.25 d, J=6 Hz, 6H), 1.20 (d, J=6 Hz, 6H). The corresponding diethyl ester was prepared in 85% yield using this procedure, but with pyridine as the base instead of dimethylaniline.

EXAMPLE 4

Ethyl p-Anisylphosphonochloridite

This and other phosphonochloridous esters were best prepared by the procedure of Steininger (Chem. Ber., 1962, 95, 2993) for the comproportionation of the corresponding phosphonous dichloride and phosphonite. Thus, a solution of diethyl p-anisylphosphonite (7.5 g, 36 mmol) in dry ether (20 mL) was added to a solution of p-anisylphosphonous dichloride (8.2 g, 36 mmol) in ether (75 mL) at 5° C. The solution was warmed to room temperature and stirred two hours, then concentrated and distilled (Kugelrohr) at 105°-110° C. (0.1 mmHg). Yield: 9.4 g (60%); IR (neat) 1595, 1500, 1255, 1095, 1025, 930, 824 cm$^{-1}$; $^1$H NMR (CDCl$_3$) δ7.9-7.5 (m, 2H), 8.1-7.8 (m, 2H), 4.0 (m, 2H), 3.82, (s, 3H), 1.30 (t, J=7 Hz, 3H); $^{31}$P NMR (CDCl$_3$) δ177.2 (ca. 90%).

EXAMPLE 5

Ethyl Phenylphosphinate

A solution of phenylphosphonous dichloride (66 g, 0.37 mol) in dry ether (100 mL) was treated dropwise with a solution of ethanol (21.6 mL, 0.37 mol) and pyridine (29.6 mL, 0.37 mol) in ether (200 mL) at room tempeature under argon. After stirring for one hour, a mixture of water (6.6 mL, 0.37 mol) and pyridine (29.6 mL) was added slowly. The reaction mixture was filtered, washed with ether, and the ether evaporated to give an oil. The oil was distilled in the Kugelrohr and then through a short Vigreux column at 95°-98° C. (0.05 mmHg); lit. (T. L. Emmick et al., J. Am. Chem. Soc., 1968, 90, 3459) 102°-103° C. (0.2 mmHg). Yield 44.3 g (70%). $^1$H NMR (CDCl$_3$)δ 7.57 (d, J=569 Hz, 1H), 8.0-7.4 (m, 5H), 4.13 (2 q, J$_{H-H}$=7 Hz, J$_{P-H}$=14 Hz, 2H), 1.35 (t, J=7 Hz, 3H).

EXAMPLE 6 p-Tolylphenylphosphine oxide

A solution of p-tolylmagnesium bromide [prepared from p-bromotoluene (29.1 g, 0.16 mol) and magnesium (4.38 g, 0.18 g-atom)] in ether (100 mL) was treated with a solution of ethyl phenylphosphonite (13,6 g, 0.08 mol) in ether (50 mL) with vigorous mechanical stirring. The mixture was heated at reflux for ½ hr., then 100 mL of 25% sulfuric acid was added cautiously. Three layers formed; the bottom (aqueous) layer was extracted with toluene. Addition of NaHCO$_3$ to the combined upper layers produced a vigorous reaction and a single organic phase. The organic phase was washed with water and with saturated NaCl, dried and evaporated to give an oil (14 g). Kugelrohr distillation at 120°-160° C. (0.1 mmHg) followed by chromatography on silica gel (CHCl$_3$), then 10% MeOH—CHCl$_3$) gave 7.1 g of an oil. This was distilled in the Kugelrohr again (150° C., 0.1 mmHg) to give 6.2 g of product which appears to be pure by NMR and crystallized on standing. $^1$H NMR (CDCl$_3$) δ8.0-7.2 (m, 9H), 8.08 (d, J=480 Hz, 1H), 2.42 (s, 3H).

EXAMPLE 7

Preparation of Phosphinited Polystyrene

A previously prepared sample of brominated polystyrene beads (Bio-Beads S-X1, 200–400 mesh) containing 17.1% bromine (27% of the rings) was used in most of the preparations. See S. E. Jacobson, et al. JACS, (1979) 101, 6938 which is hereby incorporated by reference. The polymer (3.0 g, 6.4 meq Br$^-$) was placed in an H-reactor and degassed. Into the other arm of the reactor was syringed a three-fold excess of n-butyl lithium in hexane under a stream of argon. This was concentrated on the vacuum line to about 3 mL, then about 20 mL of dry toluene was distilled onto the butyl lithium and about 10 mL of toluene onto the polymer. The n-butyl lithium solution was then filtered onto the polymer at −78° C., the mixture warmed to room temperature and then heated in an oil bath at 60° C. for 3 hrs. The suspension was then filtered through the glass frit in the H-reactor and part of the toluene was redistilled back onto the side of the polymer. After filtering again, the toluene was poured off under a stream of argon, then fresh toluene was distilled into the arm containing the polymer. The mixture was stirred briefly, then filtered, and the toluene poured out under argon. Fresh toluene (25 mL) was again distilled onto the polymer, the mixture cooled to 0° C., then treated via syringe with the phosphiniting agent (2–3 equivalents), warmed to room temperature, and stirred for one hour. The mixture was filtered and some of the toluene distilled back onto the polymer. This was stirred briefly and filtered again, then the toluene was poured off under argon. The polymer was then washed repeatedly with THF and with THF/isopropanol (1/1) in order to remove all traces of base, lithium chloride and unreacted phosphorus reagent. Inadequate washing of the polymer leads to formation of Michael adducts of acrylonitrile and alcohol in the dimerization runs. A typical analysis of the phosphinited polystyrene from a preparation using p—CH$_3$OC$_6$H$_4$P(Cl)OEt as phosphiniting agent was: C, 83.2; H, 7.90; P, 4.32; Br, 0.11. Calculated for complete replacement of bromine with p—CH$_3$OC$_6$H$_4$P(OEt): C, 81.0; H, 8.09; P, 5.3. A$^{31}$ P NMR spectrum from one of the better preparations is shown in FIG. 1a. The large broad peak in the 100–120 ppm region (relative to 85% H$_3$PO$_4$) os due to phosphinite phosphorus, by comparison to soluble reference samples. The peak at −18 ppm is due to tertiary phosphine, while the two peaks in the 20–40 ppm range are due to P(V) compounds, presumably tertiary phosphine oxide (Arbuzov rearrangement product) and perhaps phosphinate or secondary phosphine oxide. The other peaks are of unknown origin. Samples prepared using phosphonous dichlorides as the phosphiniting agent showed much larger tertiary phosphine peaks, while those prepared using phosphonites as the phosphorus reagent had very large peaks in the P(V) region.

EXAMPLE 8

Dimerization Runs

In a typical dimerization run, hexamethylbenzene, an internal standard, (800 mg, 4.93 mmol) was accurately weighted and placed in a thick-walled glass reaction vessel. To this, ca. 0.37 mmol of catalyst (monomer or polymer) listed in Table I was added and degassed on a vacuum line. Next, the following dry reagents were distilled in on a vacuum line: 1 mL of isopropanol, 3 mL of acrylonitrile, and 9 mL of toluene. Approximately 1 mL of dry cyclohexane was accurately weighted into a specially designed vessel, then transferred on the vacuum line to the reaction vessel by means of a small U-shaped tube designed to minimize the distillation path and thus facilitate accurate transfer of the internal standard. The solution was then sampled under a stream of argon so that a gas chromatogram of the starting mixture could be obtained. The reaction vessel was sealed with a high vacuum stopcock and placed in an oil bath at 60° C. At varying intervals, the reactor was removed from the bath, cooled to room temperature, and sampled under a stream of argon.

Gas chromatographic analyses were performed using the Porapak P column and a temperature program starting at 60° C., increasing at 8° C./min. for 4 min., then at 32° C./min. to 240° C. and holding for 4 min. Reference standards were prepared using cyclohexane and hexamethylbenzene as internal standards. Cyclohexane was used to calculate acrylonitrile concentration and the hexamethylbenzene was used for measuring the concentrations of methyleneglutaronitrile and the cis- and trans-1,4-dicyano-1-butene products.

EXAMPLE 9

Long-term Stability of Ethyl Di-p-tolylphosphinite

This experiment was run in the same way as described in Example 8, but a larger amount of all of the reactants was employed, except for the catalyst, Tolyl$_2$POEt. In this case, 30 mg of catalyst was used with 6 g of hexamethylbenzene, 6.7 mL of isopropanol, 7 mL of cyclohexane, 60 mL of toluene and 20 mL of acrylonitrile. A sample of this solution was sealed in an NMR tube under argon and heated together with the pressure tube at 60° C. At intervals the pressure tube was removed from the oil bath and sampled in the usual way. At the same time, the NMR tube was removed. Analysis by $^{31}$P NMR showed all of the phosphorus in the pressure tube had been converted to P(V) due to repeated openings of the tube, whereas most of the phosphorus in the NMR tube had remained in the form of P(III). The results are summarized in Table II.

EXAMPLE 10

Long-term Stability of Phosphinited Polystyrene

Attempts to run the dimerization in an H-reactor using the polymeric catalyst, ethyl p-methoxyphenylphosphinated polystyrene; filtering off the reaction solution, drying the polymer, and reusing it resulted in a rapid decline in the performance of the catalysts from one run to the next. This may be due to a number of factors, especially concentration of the dimers and oligomers in the presence of the catalyst. To avoid this problem, the dimerization was run in the same way as described in Example 8 with the soluble catalyst. Thus, 400 mg of phosphinited polystyrene was combined in a solvent reservoir with 6 g of hexamethylbezene, 6.7 mL of isopropanol, 7 mL of cyclohexane, 60 mL of toluene and 20 mL of acrylonitrile, heated at 60° C. and sampled at intervals. At the end of the experiment, the polymer was recovered and analyzed by $^{31}$P NMR spectroscopy: all of the phosphorus had been converted to P(V). The results are summarized in Table III.

TABLE I

Dimerization of Acrylonitrile to 1,4-Dicyano-1-butene[a]

| Catalyst | Time (Hr) | % Conv. | % Sel.[f] |
|---|---|---|---|
| (p-Tolyl)$_2$PO—i-Pr[b] | 3 | 28 | 85 |
| | 21 | 85 | 75 |
| Ph$_2$POEt[b] | 3 | 9[e] | 80[e] |
| | 26 | 49 | 81 |
| | 72 | 81 | 76 |
| (p-Tolyl)$_2$POEt[b] | 3 | 36 | 96 |
| | 24 | 89[e] | 91 |
| (p-Tolyl)$_2$POEt[b] | 3 | 25 | 88 |
| | 24 | 87[e] | 99[e] |
| 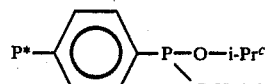 | 3 | 23 | 68 |
| | 24 | 77 | 75 |
| 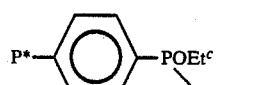 | 3 | 24 | 80 |
| | 24 | 80 | 76 |
| 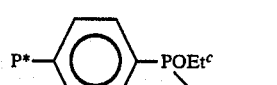 | 3 | 17[e] | 80[e] |
| | 24 | 68 | 88 |
| 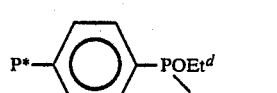 | 3 | 46 | 89 |
| | 6 | 65 | 88 |
| | 12 | 82 | 85 |
| 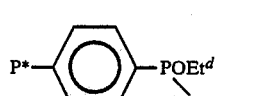 | 3 | 58 | 98 |

Footnotes to Table I
[a]Conditions: 800 mg of hexamethylbenzene, 1 mL of cyclohexane, 3 mL of acrylonitrile, 9 mL of toluene, 1 mL of i-PrOH, T = 60° C., P = 1.5 atm
[b]100 μL.
[c]200 mg.
[d]500 mg.
[e]Results at low or high high conversion are approximate due to uncertainty in integration of the G.C. peaks.
[f]% selectivity represents the yield of cis- and trans-1,4-dicyano-1-butene based on acrylonitrile consumed.
*Polystyrene cross-linked with 1 wt % divinylbenzene

TABLE II

Stability of Ethyl Di-p-Tolylphosphinite[a]

| Time (Hrs) | % Conv. | % Selec.[b] | % P(III) |
|---|---|---|---|
| 0 | — | — | 83 |
| 13 | 35 | 94 | 82 |
| 21 | 48 | 97 | 82 |
| 35 | 64 | 98 | 79 |
| 43 | 67 | 91 | — |
| 57 | 72 | 92 | 76 |
| 127 | 68 | 92 | 63 |

[a]Conditions:
0.24 mmol of catalyst, of 6.0 g of hexamethylbenzene, 7 mL of cyclohexane, 20 mL of acrylonitrile, 6.7 mL of isopropanol, 60 mL of toluene, 60° C. in a sealed NMR tube

TABLE III

Stability of Phosphinited Polystyrene[a]

| Time (Hrs) | % Conv. | % Selec.[b] |
|---|---|---|
| 19 | 20 | 67 |
| 26 | 26 | 62 |
| 44 | 36 | 62 |
| 67 | 43 | 58 |
| 91 | 47 | 53 |

[a]Conditions: 400 mg catalyst:

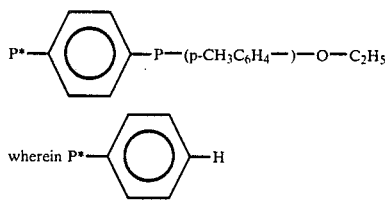

wherein P*—⬡—H is polystyrene crosslinked with 1 weight % divinylbenzene, 6.0 g of hexamethylbenzene, 7 mL of cyclohexane, 20 mL of acrylonitrile, 6.7 mL of isopropanol, 60 mL of toluene, 60° C.

[b]Selectivity represents the yield of cis- and trans-1,4-dicyano-1-butene based on acrylonitrile consumed.

EXAMPLE 11

Acrylonitrile Dimerization using Flow Reactor

This Example was run in the apparatus illustrated in FIG. 2. A flow reactor was assembled using two 0.9×30 cm glass, water-jacketed HPLC columns 13, 19, a piston-type HPLC pump 11 and a reservoir 2 fitted with stopcocks 4, 5 and a side arm 3 to allow addition of reagents with the exclusion of atmospheric oxygen and moisture. The exit of the second column 19 was attached to a pressure gauge 23, a three-way stopcock 25 and a graduated receiver 27. The inlet tube 26 to the receiver 27 was attached via a side arm to a mercury bubbler (not shown) which allowed application of 30 cm Hg pressure to the system. At least 20 cm Hg pressure is necessary to prevent bubble formation in the reactor columns 19 and dry columns 13 and 16.

The two columns were fitted with adjustable plungers and stopcocks at each end. A three-way stopcock 17 was used at the bottom (inlet) end of the column 19 holding the catalyst resin. The two columns were dried at 150° C., then placed while still hot in the port of a dry box. In the dry box, one column 13 was charged with 10 g of 16 mm pellets of 3A molecular sieves which had been activated at 200° C. while being evacuated on a vacuum line, then allowed to cool under dry argon. The second column 19 was charged with 2.0 g (2.9 mmol of phosphorus) of the ethyl p-methoxyphenylphosphinite polystyrene catalyst bearing previously described in Example 10. Both columns were closed and removed from the dry box, then attached to the remainder of the system. Column 16 was not used in this experiment.

The solvent reservoir was filled, under argon, with a degassed and dry solvent mixture of diisopropyl phenylphosphonite (20 μL), toluene (50 mL) and isopropanol (5 mL).

The solvent mixture was pumped through the columns at a rate of 22 mL/hr. until all bubbles of argon had been removed, then the water circulating bath was turned on, the system pressurized to 30 cm Hg and the temperature of the columns 13, 19 raised to 60° C. The catalyst resin had swollen to about 13 mL volume.

In a specially designed reagent vessel 1, was placed 150 μL diisopropyl phenylphosphonite. The flask was attached to a vacuum line and the following dry reagents distilled in: toluene (270 mL), isopropanol (27 mL), cyclohexane (20.6 g, 26 mL) and acrylonitrile (67.8 g, 84 mL).

Vessel 1 was filled with argon, warmed to room temperature and the reagents thoroughly mixed. Vessel 1 was then attached to reservoir 2 via the sidearm 8 which was repeatedly evacuated and filled with argon. The reservoir 2 was evacuated and the contents of flask B transferred to it by opening the stopcock 9 above the filter 10. Pumping speed was adjusted to 7.8 mL/hr and this point was designated as time 0 hr.

The effluent from the reactor was collected in 125 mL graduated receivers 27 which were changed periodically at intervals of 10-13 hrs. Evaporation of each of these samples at 35° C. (1 mm Hg) left an oil which consisted of the acrylonitrile dimers and higher oligomers. The samples were further analyzed by gas chromatography and by Kugelrohr distillation of the dimers [linear and branched at 80°-100° C. (0.1 mm Hg)]. Percent selectivities to dimers (see Table IV) were 90-91% a mixture of dimers (92% linear vs 8% branched dimers).

At intervals, samples of the reaction mixture were taken using the three-way stopcocks 17 and 25 before and after the catalyst bed. Gas chromatographic analysis of the amount of acrylonitrile present relative to cyclohexane allowed calculation of the percent conversion. The percent conversion slowly declined during the experiment from 63% initially to 40% at 184 hours (see FIG. 2).

Additional batches of the reagent mixture were prepared and transferred to the reservoir when needed. Percent conversions were measured for periods when the flow rate was 7.7±0.1 mL/hr.

Figure 3:
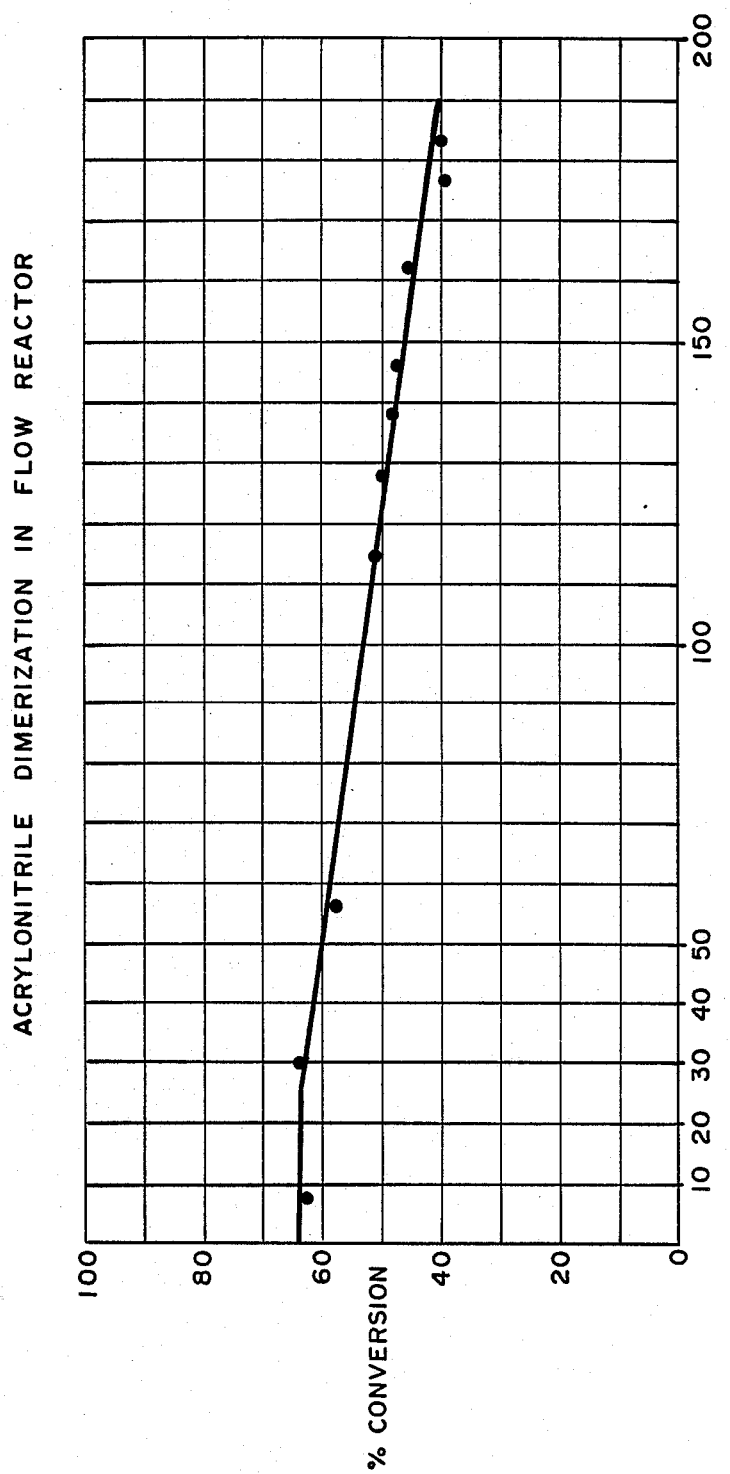
FIG. 3 graphically illustrates the variation in the percent conversion of ACN vs reaction time for the polymer-bound phosphinite catalyst of the present invention operated as shown in FIG. 2.

At 184 hours the last reservoir of reagents had been consumed and a mixture of toluene:isopropanol (10:1) was added to purge all of the remaining reagents through the system. The combined collected fractions contained 109.64 gm of products, equivalent to 2.066 moles of acrylonitrile converted. This represents 714 catalyst turnovers. Results are summarized in Table IV and FIG. 3.

After about 30 hours of reaction, the pump had to be disconnected and a valve was changed. After replacement of the valve and reconnection of the pump, the reaction was continued but the percent conversion started to decline faster. It is believed that this interruption caused contamination of the catalyst by moisture and oxygen. It is further believed that if this interruption had not occurred and if the reagent mixture had been more effectively dried such as by use of polystyrene-bound dialkylphosphonite (e.g., placed in column 16 as shown in FIG. 2), the decline in the activity of the catalyst as measured by the percent conversion would have been lower.

TABLE IV

Acrylonitrile Dimerization Products

| Receiver | Vol. mL | Wt g | (residue)[a] Wt. g | (dimers)[b] Wt. g | % Selec.[c,d] to dimers |
|---|---|---|---|---|---|
| 1 | 103 | 88.9 | 9.76 | 8.87 | 91 |
| 2 | 98.5 | 86.2 | 10.91 | | |
| 3 | 84.5 | 73.2 | 9.14 | | |
| 4 | 84 | 72.5 | 8.09 | 7.33 | 91 |
| 5 | 80 | 68.7 | 7.11 | | |
| 6 | 73 | 62.8 | 6.62 | | |
| 7 | 77.5 | 67.5 | 7.01 | 6.31 | 90 |
| 8 | 80 | 68.6 | 6.86 | | |
| 9 | 98 | 84.7 | 7.79 | | |
| 10 | 80 | 67.5 | 6.01 | 5.45 | 91 |
| 11 | 91 | 78.2 | 6.82 | | |

TABLE IV-continued

| | | | Acrylonitrile Dimerization Products | | |
|---|---|---|---|---|---|
| Receiver | Vol. mL | Wt g | (residue)[a] Wt. g | (dimers)[b] Wt. g | % Selec.[c,d] to dimers |
| 12 | 73 | 62.6 | 5.32 | | |
| 13 | 94 | 80.3 | 5.22 | 5.57 | 90 |
| 14 | 94 | 80.4 | 5.97 | | |
| 15 | 120 | | 4.92 | | |
| Combined samples | | | 1.09 | | |
| Total | | | 109.64 | | |

[a]After evaporation of reagents at 35° C. (1 mm Hg)
[b]Isolated by Kugelrohr distillation at 80–100° C. (0.1 mm Hg).
[c]92% 1,4-dicyano-1-butenes, 8% methyleneglutaronitrile.
[d]% Selectivity to DCB-1 = % Selec. to dimers × 92% (% DCB-1 in dimers).

EXAMPLE 12

Preparation of the polystyrene-bound phosphonous dichloride (P)—$C_6H_4$—$PCl_2$ In a typical preparation, 1 gm (9.6 mmol) polystyrene resin cross-linked with 1 weight % divinylbenzene (Bio Beads. S-X1, 200–400 mesh) and 1.33 gm (100 mmol) anhydrous aluminum chloride ($AlCl_3$) were placed under an inert atmosphere into one side of an "H"-reactor, as described in Example 7, and equipped with a reflux condenser with an argon inlet; 12.5 mL (excess) of degassed $PCl_3$ were syringed, under a stream of argon, into the reactor which was then placed in an oil bath at 60° C. and stirred for 3 hours. The reaction mixture was degassed and filtered through the coarse glass frit and the filtrate poured off under argon. The polymer product was washed extensively with dry THF to remove residual $AlCl_3$ and dried in vacuo; yield 1.7 gm, $^{31}P$ NMR (swollen in $CH_2Cl_2$) δ162 ppm (phosphonous dichloride). Phosphorus, 13.0% by weight, was incorporated into polymer indicating that ca. 75% of the rings were functionalized.

EXAMPLE 13

Preparation of the polystyrene-bound diisopropyl phosphonite

One gram (4.9 mmol) of the phosphonous dichloride was charged under an inert atmosphere into an "H"-reactor which was then evacuated on the vacuum line. Fifteen mL of dry pyridine were distilled onto the polymer and 1.2 mL (147 mmol) of dry isopropanol were distilled into the opposite leg of the reactor. The polymer suspension was stirred at 0° C. for 1 hour while the ispropanol slowly distilled over. The mixture was warmed to room temperature and stirred an additional hour. The reaction was filtered through a glass frit, and the the filtrate was poured off under argon. The polymer was washed repeatedly with dry methylene chloride and dried in vacuo. The $^{31}P$ NMR spectrum contained a peak at 162 ppm (broad peak) indicative of phosphonite phosphorus.

EXAMPLE 14

This example illustrates the use of polystyrene-bound diisopropyl phosphonite of Example 13 as a drying agent in acrylonitrile dimerization using the flow reactor of Example 11. A water-jacketed HPLC column 16 is placed in line 15 after column 13 and before the catalyst column 19 of FIG. 2. The procedure of Example 11 is followed. A lower decline in the % conversion after a longer reaction time is expected due to a more complete removal of water.

EXAMPLE 15

Preparation of polystyrene-bound 3,4,5-trimethylphenyl phosphinous chloride

One gram (4.9 mmol) of the Polystyrene-bound phosphonous dichloride and 0.72 gm (5.4 mmol) of $AlCl_3$ were charged under an inert atmosphere into an H-reactor equipped with a reflux condenser with an argon inlet. Fifteen mL (excess) of 1,2,3-trimethylbenzene were syringed in under a stream of argon and suspension was stirred at 60° C. for 6 hours. The filtrate was poured off under argon, and the polymer was washed with dry THF, then with THF/pyridine in the ratio of 15/2 and dried in vacuo. The $^{31}P$ NMR spectrum contained a peak at 85 ppm (phosphinous chloride phosphorus), and a smaller peak due to dichloride at 162 ppm. In another experiment, the H-reactor was charged as described above and the suspension was stirred under a stream of argon at 100° C. for 1 h. The polymer was washed and dried as described above. The $^{31}P$ NMR spectrum indicated that ca. 95% of the phosphorus was in the form of phosphinous chloride (peak at 85 ppm) and that only ca. 5% of unreacted starting material was present (peak at 162 ppm).

EXAMPLE 16

Preparation of the polystyrene-bound isopropyl 3,4,5-trimethylphenyl phosphinite One gram of the phosphinous chloride prepared as described in Example 15 was charged into an H-reactor under an inert atmosphere and evacuated on the vacuum line. 15 mL of dry THF and 0.5 mL of dry pyridine were distilled onto the polymer and 0.5 mL (6.1 mmol) of dry isoprpanol was distilled into the opposite leg. The reaction conditions of Example 13 were followed. The polymer was washed extensively with dry THF. The $^{31}P$ NMR spectrum contained a peak at 107 ppm indicative of phosphinite phosphorus (ca. 90% of P) and a smaller peak at 44 ppm (ca. 10% of P) due to an unidentified impurity. See FIG. 1b.

EXAMPLE 17a

Reaction 3,4,5-$(CH_3)_3C_6H_2PCl_2$ and Polystyrene at 60° C.

One gram (9.6 mmol) of polystyrene resin cross-linked with 1% divinylbenzene (Bio Beads, S-Xl, 200–400 mesh) and 1.33 gm (10.0 mmol) $AlCl_3$ were charged under an inert atmosphere into a H-reactor equipped with a reflux condenser and argon inlet. The polymer was swollen in 10 mL of dry 1,1,2,2-tetrachloroethane which was added (syringe) under argon. 3,4,5-$(CH_3)_3C_6H_2PCl_2$ (2.8 gm, 12.7 mmol) dissolved in 2 mL dry 1,1,2,2-tetrachloroethane was added to reaction mixture via syringe under argon and the reaction mixture so formed was heated at 60° C. for 4 hours. The suspension was degassed and filtered through the glass frit, and the filtrate poured off under argon. The polymer was washed extensively with dry THF. The $^{31}P$ NMR spectrum showed no incorporation of phosphorus into the polymer.

EXAMPLE 17b

Reaction of 3,4,5-$(CH_3)_3$—$C_6H_2PCl_2$ with Polystyrene at 100° C.

The reaction described in Example 17a was repeated excepting that the reaction mixture so formed was heated at 100° C. for 2 hours. The dark brown reaction mixture produced was filtered under argon and a red brown solid recovered and washed three times with 15 mL portions of THF. The yellow-orange solid was washed with dry $CH_2Cl_2$, again with THF (the color of solid remained unchanged) and dried in vacuo to give a gummy yellow-orange solid. The $^{31}P$ NMR analysis on the gummy solid swollen in $CH_2Cl_2$ gave a spectrum consisting of a large broad multiplet of unassigned peaks at 70 ppm, 51.4 ppm, 46 ppm and 36 ppm, said unassigned peaks indicative of incoporation of phosphorus into polymer and a small peak at 162 ppm; indicative of a phosphonous dichloride. There was no peak at 85 ppm indicative of uncomplexed polymer-bound phosphinous chloride.

EXAMPLE 17c

Attempted Preparation of Poly-styrene-bound Isopropyl 3,4,5-trimethylphenyl phosphinite The reaction product of Example 17b was treated in accordance with the apparatus and procedure of Example 16. Dry THF and pyridine were distilled into ca. 700 mg of the gummy yellow-orange solid of Example 17b and removed by filtration. Fresh dry THF (12 mL) dry pyridine (2 mL) and dry isopropanol (2.0 mL) were distilled onto polymer. The reaction conditions and apparatus of Example 13 were then used excepting that the reaction product was washed with THF and a THF-isopropanol mixture and dried in vacuo. There was recovered 0.53 g of a yellow-orange gummy solid. The $^{31}P$ NMR spectrum contained a broad multiplet of peaks centered around 30 ppm indicative of phosphorus (V). The phosphorus signal was very weak, indicating little phosphours was incorporated and the spectrum contained no peak around 110 ppm indicating no phosphinite phosphorus was present.

EXAMPLE 18

Trimethylsilyl dibutylphosphinite

The procedure described in *Tetrahedron*, 1967, 23, 1065 (M. Grayson et al.) was followed. Dibutylphosphine oxide, prepared from butyl magnesium bromide and diethylphosphite, (3.3 g, 20 mmol) and triethylamine (2.02 1 g, 20 mml) were dissolved in toluene (20 mL) and treated with a solution of trimethylsilyl chloride (2.17 g, 20 mmol) in toluene (5 mL) at room temperature. The solution got very warm and a precipitate formed immediately. The mixture was heated at 80° C. for two hours, then filtered, washed with toluene, and concentrated. Kugelrohr distillation a 80° C. (1.5 mmHg) afforded 4.1 g (86%) of the desired product. $^1H$ NMR ($CDCl_3$) $\delta$1.8–1.2 (m, 6H), 1.1–0.7 (m, 3H), 0.17 (s, 9H).

EXAMPLE 19

Attempted Dimerization of ACN using Trimethylsilyl Dibutylphosphinite

A dimerization reaction mixture was prepared in accordance with the apparatus and procedure of Example 8 from cyclohexane (1 mL), isopropanol (1 mL), acrylonitrile (3 mL), toluene (9 mL), hexamethylbenzene (1.334 g) and trimethylsilyl dibutylphosphonite (0.1 mL) of Example 18. The solution was heated at 60° C. for 18 hrs, then sampled under argon. GC analysis showed no reaction products and no conversion of the acrylonitrile. Analysis of the reaction mixture by $^{31}P$ NMR showed one major peak at $\delta$46 ppm, corresponding to a rearrangement product, and nothing at 117 ppm relative to 85% $H_3PO_4$ where the starting phosphinite phosphorus appears.

EXAMPLE 20

4-(2-Hydroxypropyl)polystyrene

A 3.0 g sample of brominated polystyrene containing 29% bromine and crosslinked with 1% of divinylbenzene was placed on one side of an H-reactor. Butyl lithium (20 mL, 2.4M) was syringed into the other side, the hexane solvent was mostly evaporated and replaced by 30 mL dry toluene. The toluene solution was filtered onto the polymer and the mixture was heated at 60° C. for 3 h. The polymer was filtered, the toluene poured off and fresh toluene distilled in. After several washings the toluene was poured off and the polymer dried. Fresh toluene (30 mL) was then distilled onto the polymer followed by 1.1 mL of propylene oxide (15.7 mmol). The mixture was stirred at room temperature for 20 h., then filtered, the solvent poured off and 20 mL of isopropanol were distilled in. After stirring, the polymer was filtered again and then washed in the air with isopropanol (2×100 mL), isopropanol containing several drops of concentrated hydrochloric acid (2×100 mL) and again with isopropanol (2×100 mL). Drying overnight in a vacuum oven at 60° C. gave 2.5 g of product. Analysis for hydroxyl content gave a value of 3.7 meq OH/g of polymer.

EXAMPLES 21–22

Partially Phosphinited Hydroxypropylpolystyrene

A 1.0 g sample of the hydroxypropylpolystyrene prepared as described in Example 20 was treated in an H-reactor with di-p-tolylphosphinous chloride (0.37 g, 1.49 mmol) in pyridine (15 mL). After 3 days the mixture was filtered, washed with pyridine once and with dichloromethane several times. The dried polymer weighed 0.95 g. Phosphorus NMR Spectrum contained only a single broad peak at ca. $\delta$107 ppm. Finally phosphinited hydroxypropylpolystyrene was prepared similarly using an excess of phosphinous chloride. The $^{31}P$ NMR spectrum contained only a single broad peak at ca. $\delta$107 ppm.

EXAMPLE 23

Partial Phosphination of TDI-Cross-linked PVAL

A sample of polyvinyl alcohol cross-linked with about 5% tolylenediisocyanate was dried in vacuo at 60° C. The polymer (0.33 g) was placed in an H-reactor and treated with diphenylphosphinous chloride (0.50 g, 2.25 mmol) in pyridine (15 mL) for 4 days at room temperature. After filtration, the polymer was washed several times with dichloromethane and dried. Yield: 0.23 g. Phosphorus NMR showed a substantial amount of phosphorus incorporation, with about 90% in the phosphinite form. The sample was recovered from the NMR tube, dried and used in a dimerization run (See Example 28) but no conversion of ACN was observed. (See Table V).

EXAMPLE 24

Complete Phosphination of TDI-Cross-linked PVAL

A 0.5 g sample of dried, 5% TDI-cross-linked, 80% hydrolyzed polyvinyl acetate was treated with a slight excess of di-p-tolylphosphinous chloride (2.0 g, 8 mmol) in pyridine (15 mL) for 4 days at room temperature. The polymer was filtered, washed with dichloromethane and dried. Yield: 0.49 g. The phosphorus NMR spectrum showed a strong peak in the region (δ110 ppm) expected for phosphinite and a smaller peak in the P(V) region. Thus, although there was no weight gain, the recovered material contained an appreciable amount of phosphorus. This polymer was used in a dimerization reaction with neopentyl alcohol. (See Example 28). No conversion of ACN was indicated by GLC.

EXAMPLE 25

Fully Phosphinited TOYOPEARL ®

A 1.0 g of dried, coarse TOYOPEARL ® was treated with excess di-p-tolylphosphinous chloride (2.5 g, 10 mmol) in pyridine (20 mL) in an H-reactor. After 2 days at room temperature the reaction was stopped. The mixture could not be filtered, so the pyridine was pumped off and dichloromethane distilled in. The polymer was stirred briefly, then filtered. After several more washings with dichloromethane, the product was dried on the vacuum line. An appreciable amount of material was lost due to the fine particles being pulled up into the vacuum line. Yield: 1.45 g. The $^{31}$P NMR spectrum showed a strong broad peak at δ115 ppm phosphinite phosphorus and a number of sharp resonances of lower intensities due to monomeric phosphorus species.

EXAMPLE 26

Partially Phosphinited TOYOPEARL ® (30%)

Superfine TOYOPEARL ® (3.0 g) was treated with about 0.3 equivalents of di-p-tolylphosphinous chloride (1.4 g) in pyridine for 2 days at room temperature. The product was filtered in a glove bag and washed with dichloromethane, then dried overnight in a vacuum oven. It was then washed repeatedly with dichloromethane in an H-reactor and redried. Yield: 2.7 g. Phosphorus NMR shows a broad peak in the phosphinite region and a smaller broad peak in the P(V) region.

EXAMPLE 27

Partially Phosphinited TOYOPEARL ® (6%)

A 4.0 g sample of coarse TOYOPEARL ® was treated with about 0.06 equivalents of di-p-tolylphosphinous chloride (0.44 g, 1.77 mmol) in pyridine (30 mL). The mixture was stirred overnight at room temperature, filtered under argon and washed with dichloromethane, then dried on the vacuum line. Yield: 4.35 g. The phosphorus NMR showed a single broad resonance at δ115 ppm (due to phosphinite phosphorus) and a small amount of a monomeric P(V) compound.

COMPARATIVE EXAMPLE 28

Dimerizations of acrylonitrile using hydroxylcontaining polymer-bound phosphinites of Examples 21–27 were run in accordance with the procedure of Example 8 excepting that no isopropanol was added. In runs 6–7 wherein all the OH groups of polymer-bound catalyst were converted into phosphinite at the start of the reaction, neopentyl alcohol was added. See Table V for a summary of results.

ACN Dimerization Runs 6–8 of Example 28

Dimerization using Fully Phosphinited Toyopearl and Neopentyl Alcohol

A dimerization reaction was carried out in accordance with the procedure and apparatus of Example 8 using the fully phosphinited TOYOPEARL of Example 25 as the catalyst and neopentyl alcohol as the added alcohol. After 20 h, the reaction mixture was analyzed. Conversion was 90% and selectivity to 1,4-dicyano-1-butenes also about 90%. The reaction mixture was filtered, concentrated and the phosphorus NMR Spectrum was obtained on a methylene chloride solution of the residue. The $^{31}$P NMR spectrum showed several peaks, the major ones being at δ112 ppm, due to neopentyl di-p-tolylphosphinite, and at δ29 ppm, probably due to the tertiary phosphine oxide. The $^{31}$P NMR spectrum of the recovered polymer showed no polymerbound phosphorus. Repetition of the experiment gave 14% conversion after 3 h, with >90% selectivity; in addition to the peaks noted above, the $^{31}$P NMR showed a smaller peak at δ−50 ppm due to the pentacoordinate phosphorane.

TABLE V

ACN Dimerization Runs Using Various Polymer-Bound Phosphinite Without Added Alcohol[a]

| | Polymer[b] | % P[c] | Time (Hr.) | Results |
|---|---|---|---|---|
| 1 | PS—OP—Tolyl$_2$[1] | 40 | 22.5 | No ACN conversion |
| 2 | PS—OP—Tolyl$_2$[1] | 40 | 5 | Mainly P(V) |
| 3 | PS—OP—Tolyl$_2$[1] | 5 | 24 | No ACN conversion |
| 4 | TDI-PVAL[3] | 40 | 6 | No ACN conversion |
| 5 | TDI-PVAL[4] | 100 | 24 | No ACN conversion |
| 6 | TOYOPEARL ®[5] | 100[d] | 20 | 90% conversion; 90% selectivity to DCB-1; No polymer-bound phosphorus after 20 hrs; neopentyl di-p-tolylphosphinite present |
| 7 | TOYOPEARL ®[5] | 100[d] | 3 | 14% conversion; 90% Selectivity to DCB-1; No polymer-bound phosphorus after 3 hrs; neopentyl di-p-tolyl-phosphonite and P(V) present |
| 8 | TOYOPEARL ®[6] | 6 | 24 | 11% conversion; 37% selectivity to DCB-1 |

[a] 60° C. Typical amounts: 9 mL of toluene, 3 mL of ACN, 1 mL of cyclohexane, 0.2 mmol of phosphorus.
[b] PS—O = 4-(2′-hydroxy-1′-propylpolystyrene crosslinked with 1% of divinylbenzene. (See Examples 21–22); TDI-PVAL = 5% Tolylene diisocyanate cross-linked polyvinyl alcohol.
[c] Percent of polymer-bound OH groups derivatized with P—(p-CH$_3$C$_6$H$_5$) groups.
[d] Neopentyl alcohol was added.

Preparation of Polymers listed in Table V

1. See Examples 21, 22.
2. See Examples 21, 22.
3. See Examples 23.
4. See Examples 24.
5. See Examples 25.
6. See Examples 27.

We claim:

1. A heterogeneous catalytic process for converting acrylonitrile into 1,4-dicyano-1-butene which comprises contacting a liquid phase comprising acrylonitrile with an effective amount of polymer-bound alkyl diarylphosphinite catalyst which is solid under process conditions for a time sufficient to effect conversion of acrylonitrile into 1,4-dicyano-1-butene, wherein said catalyst has the formula:

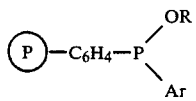

wherein:
- Ⓟ represents polystyrene crosslinked with at least about 1% of divinylbenzene;
- —C₆H₄ represents a phenylene ring derived from and bound to said solid polymer of styrene;
- —OR represents an alkoxy group wherein R is alkyl straight chain or branched, having 1-10 carbons, or cycloalkyl having 5-10 carbons;
- —Ar represents an aryl group having the formula

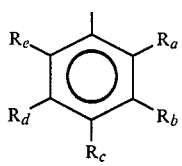

wherein $R_a$ through $R_e$ are independently selected from the group consisting of:
(a) hydrogen;
(b) alkyl, straight chain or branched, having 1-10 carbons;
(c) cycloalkyl, having 5-10 carbons;
(d) —OR³, wherein R³ represents alkyl having 1-10 carbons or cycloalkyl having 5-10 carbons; and
(e) —N(R⁴R⁵) wherein R⁴ and R⁵ are independently alkyl, straight chain or branched, having 1-10 carbons or cycloalkyl having 5-10 carbons;
wherein two of said $R_a$ through $R_e$ groups may form part of a fused alicyclic ring.

2. The process of claim 1 wherein the contacting is performed under substantially anhydrous and oxygen-free conditions.

3. The process of claim 1 wherein at least 5 percent of phosphorus in the polymer-bound alkyl diarylphosphinite catalyst is present as phosphinite.

4. The process of claim 1 wherein the contacting is performed in the substantial absence of bases and lithium cations.

5. The process of claim 1 wherein the contacting is performed in a flow reactor.

6. The process of claim 1 wherein the polymer of said polymer bound catalyst consists essentially of polystyrene cross-linked with at least about 1% of divinylbenzene.

7. The process of claim 6 wherein the catalyst is Ⓟ—C₆H₄—P((CH₃)₃C₆H₂—)OR.

8. The process of claim 7 wherein R is cyclohexyl or R¹R²C(H)— wherein R¹ and R² are independently hydrogen or straight or branched chain alkyl groups having 1 to 9 carbon atoms.

9. The process of claim 6 wherein the catalyst is Ⓟ—C₆H₄—P—(p—CH₃OC₆H₄—)OR.

10. The process of claim 9 wherein R is cyclohexyl or R¹R²C(H)— wherein R¹ and R² are independently hydrogen or straight or branched chain alkyl groups having 1 to 9 carbon atoms.

11. The process of claim 1 wherein the liquid acrylonitrile phase further comprises an inert solvent and a proton-donating solvent and wherein the total water content of the liquid phase is less than about 50 ppm.

12. The process of claim 11 wherein the liquid phase, prior to contacting same with said polymer-bound phosphinite catalyst, is treated with an effective amount of a drying agent comprising polymer-bound dialkyl arylphosphonite for a time sufficient to reduce the total water content of the liquid phase to a value less than about 15 ppm.

13. The process of claim 12 which further comprises recovering the drying agent comprising polymer-bound alkyl phosphinate having the formula Ⓟ—C₆H₄—P=O(OR)(H) produced by the interaction of the polymer-bound dialkyl arylphosphonite with water in the liquid phase, recovering and contacting said phosphinate with an effective amount of PCl₃ for a time sufficient to produce a polymer-bound alkyl arylphosphonous dichloride and contacting said polymer-bound alkyl arylphosphonous dichloride with a primary or secondary alkanol of 1-10 carbons in the presence of base for a time sufficient to produce polymer-bound dialkyl arylphosphonite.

14. The process of claim 12 wherein the drying agent is polystyrene-bound diisopropyl arylphosphonite.

15. The process of claim 11 wherein the liquid acrylonitrile phase further comprises isopropanol and toluene.

16. The process of claim 1 wherein the aryl group, —Ar, is substituted with at least two straight or branched chain alkyl group having one to ten carbon atoms.

* * * * *